United States Patent
Siddiqui et al.

(10) Patent No.: US 11,643,395 B2
(45) Date of Patent: May 9, 2023

(54) DERIVATIVES OF 4-AMINOANTIPYRINE AS ANTI-ALZHEIMERS BUTYRYLCHOLINESTERASE INHIBITORS

(71) Applicants: Hina Siddiqui, Karachi (PK); Muhammad Iqbal Choudhary, Karachi (PK); Atia-tul- Wahab, Karachi (PK); Atta-ur- Rahman, Karachi (PK); Fazila Rizvi, Karachi (PK); Sheeba Wajid, Karachi (PK)

(72) Inventors: Hina Siddiqui, Karachi (PK); Muhammad Iqbal Choudhary, Karachi (PK); Atia-tul- Wahab, Karachi (PK); Atta-ur- Rahman, Karachi (PK); Fazila Rizvi, Karachi (PK); Sheeba Wajid, Karachi (PK)

( * ) Notice: Subject to any disclaimer, the term of this patent is extended or adjusted under 35 U.S.C. 154(b) by 0 days.

(21) Appl. No.: 17/396,799

(22) Filed: Aug. 9, 2021

(65) Prior Publication Data
US 2021/0363108 A1  Nov. 25, 2021

(51) Int. Cl.
C07D 231/48  (2006.01)
(52) U.S. Cl.
CPC ................................. C07D 231/48 (2013.01)
(58) Field of Classification Search
CPC .................................................... C07D 231/48
See application file for complete search history.

(56) References Cited

U.S. PATENT DOCUMENTS

| 4,295,853 | A | * | 10/1981 | Kasahara | ............. | C07D 231/48 436/66 |
| 7,582,123 | B2 | * | 9/2009 | Fadli | .................... | C07D 231/48 8/405 |

\* cited by examiner

*Primary Examiner* — Kamal A Saeed

(57) ABSTRACT

One embodiment of the invention relates to the treatment of diseases associated with increased butyrylcholinesterase (BuChE) enzyme activity such Alzheimer's Disease (AD), involving administering an effective amount of a compound selected from a group of new N, N'-disubstituted benzylamine derivatives (1-8) of 4-aminoantipyrine (ampyrone). The kinetic studies of two potent compounds 4-(Bis(4-iodobenzyl) amino)-1,5-dimethyl-2-phenyl-1,2-dihydro-3H-pyrazol-3-one (5) ($IC_{50}$=2.43±0.4 and Ki=5.67±0.5 µM) and 4-(Bis(2-bromobenzyl) amino)-1,5-dimethyl-2-phenyl-1,2-dihydro-3H-pyrazol-3-one (6) ($IC_{50}$=0.7±0.2 and Ki=2.4±0.4 µM), revealed them as a competitive and a non-competitive inhibitor of BuChE, respectively. Galantamine Hydrobromide was used as standard inhibitor with $IC_{50}$=40.83±0.4 and Ki=21.5±0.7 µM (Mixed type Inhibitor). The metabolite of aminophenazone, 4-aminoantipyrine (A) is also being reported here as an inhibitor of BuChE for the first time.

3 Claims, No Drawings

DERIVATIVES OF 4-AMINOANTIPYRINE AS ANTI-ALZHEIMERS BUTYRYLCHOLINESTERASE INHIBITORS

BACKGROUND OF THE INVENTION

4-Aminoantipyrine (A) is a metabolite of aminophenazone (drug being used as anti-inflammatory in the past. Which was withdrawn due to its adverse effects of agranulocytosis), is an aromatic compound with analgesic, antipyretic, and anti-inflammatory properties. The pharmacological activities of 4-Aminoantipyrine (A) derivatives includes analgesic, antimicrobial, and antiviral properties.

The current study relates to the synthesis of eight new N, N'-disubstituted benzylamine derivatives of 4-aminoantipyrine (A), and evaluation of their in vitro BuChE inhibition activity.

Alzheimer's disease (AD) is an acute neurological disorder, which causes behavioral and cognitive dysfunctions. The disease is managed by the inhibition of cholinesterase (ChE) enzymes, acetylcholinesterase (AChE) and butyrylcholinesterase (BuChE). In a healthy brain acetylcholinesterase (AChE) plays a major role while butyrylcholinesterase (BuChE) is known for the minor role. However, in Alzheimer's Disease (AD) the increased level of (BuChE) found with the decline or unchanged level of AChE activity. Therefore, butyrylcholinesterase (BuChE) inhibitors are used as possible treatment of AD.

Donepezil, galanthamine, and rivastigmine are frequently used inhibitors of cholinesterase (ChE) enzymes. These inhibitors are associated with several side effects such as, diarrhea, insomnia, anorexia, weight loss, and esophageal rupture.

BRIEF SUMMARY OF THE INVENTION

The present invention relates to the synthesis of eight new derivatives of 4-aminoanitpyrine (A) and evaluation of their BuChE inhibition activity. The newly synthesized compounds were found to be the potent in vitro inhibitors of (BuChE) enzyme, in comparison with the standard drug galantamine hydrobromide ($IC_{50}$=40.83±04 µM). which can be further studied for the management and treatment of AD.

DETAILED DESCRIPTION OF THE INVENTION

Synthesis: N, N'-Disubstituted benzylamine derivatives of 4-aminoantipyrine (A) 1-8 were synthesized through microwave reactor in 1-3 min at 220° C., and power 900 W, in the presence of base $K_2CO_3$ and substituted benzyl bromide in 2 mL DMF as describe in following reaction scheme.

Reaction Scheme:

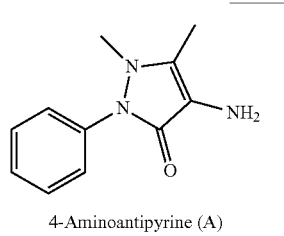

4-Aminoantipyrine (A)

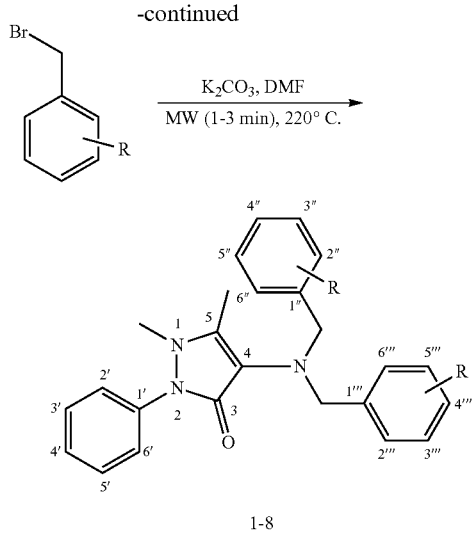

1-8

4-(Bis(3-chlorobenzyl) amino)-1,5-dimethyl-2-phenyl-1,2-dihydro-3H-pyrazol-3-one (1): Mp: 200-201° C.; IR (KBr, $cm^{-1}$): 1654 (C=O), 1592, 1488 (C=C), 1083.1 (C—Cl); EI-MS (direct probe, positive EI) m/z: 453.2 $[M+2]^+$, 451.2 $[M^+]$, 326.1; HREI-MS m/z: Calculated for $C_{25}H_{23}Cl_2N_3O$: 451.1218, Observed: 451.1224; $^1$H-NMR (400 MHz, DMSO-$d_6$) δ: 7.45 (t, $J_{5'',4''/5'',6''}=J_{5''',4'''/5''',6'''}$=8 Hz, 2H, H-5", H-5'''), 7.29 (ovp, 11H, H-2', H-3', H-4', H-5', H-6', H-2", H-4", H-6", H-2''', H-4''', H-6'''), 4.13 (s, 4H, 2CH$_2$), 2.74 (s, 3H, N—CH$_3$), 1.71 (s, 3H, CH$_3$).

4-(Bis(2-chlorobenzyl) amino)-1,5-dimethyl-2-phenyl-1,2-dihydro-3H-pyrazol-3-one (2): Mp: 211-212° C.; IR (KBr, $cm^{-1}$): 1653 (C=O), 1590, 1529 (C=C), 1046 (C—Cl); EI-MS (direct probe, positive EI) m/z: 453.2 $[M+2]^+$, 451.2 $[M^+]$, 326.1; HREI-MS m/z: Calculated for $C_{25}H_{23}Cl_2N_3O$: 451.1218, Observed: 451.1204; $^1$H-NMR (400 MHz, DMSO-$d_6$) δ: 7.47 (t, $J_{3',2'/3',4'}=J_{5',4'/5',6'}$ 8 Hz, 2H, H-3', H-5'), 7.37 (m, 4H, H-2', H-6', H-3", H-3'''), 7.28 (m, 7H, H-4', H-4"-H-6", H-4'''-H-6'''), 4.27 (s, 4H, 2CH$_2$), 2.71 (s, 3H, N—CH$_3$), 1.50 (s, 3H, CH$_3$).

4-(Bis(3-iodobenzyl) amino)-1,5-dimethyl-2-phenyl-1,2-dihydro-3H-pyrazol-3-one (3): Mp: 203-204° C.; IR (KBr, $cm^{-1}$): 1648 (C=O), 1619, 1590 (C=C), 849.8 (C—I); EI-MS (direct probe, positive EI) m/z: 635.3 $[M^+]$, 508.3, 417.9; HREI-MS m/z: Calculated for $C_{25}H_{23}I_2N_3O$: 634.9930, Observed: 634.9943; $^1$H-NMR (400 MHz, DMSO-$d_6$) δ: 7.61 (s, 2H, H-2", H-2'''), 7.57 (d, $J_{4'',5''}=J_{4''',5'''}$=5.4 Hz, 2H, H-4", H-4'''), 7.46 (t, $J_{3',2'/3',4'}=J_{5',4'/5',6'}$=8 Hz, 2H, H-3', H-5'), 7.27 (m, 5H, H-2', H-4', H-6', H-6", H-6'''), 7.10 (t, $J_{5'',4''/5'',6''}=J_{5''',4'''/5''',6'''}$=7.8 Hz, 2H, H-5", H-5'''), 4.08 (s, 4H, 2CH$_2$), 2.74 (s, 3H, N—CH$_3$), 1.66 (s, 3H, CH$_3$).

4-(Bis(2-iodobenzyl) amino)-1,5-dimethyl-2-phenyl-1,2-dihydro-3H-pyrazol-3-one (4): Mp: 221-222° C.; IR (KBr, $cm^{-1}$): 1653 (C=O), 1615, 1589, (C=C), 838.1 (C—I); EI-MS (direct probe, positive EI) m/z: 635.3 $[M^+]$, 508.3, 417.9; HREI-MS m/z: Calculated for $C_{25}H_{23}I_2N_3O$: 634.9930, Observed: 634.9959; $^1$H-NMR (400 MHz, DMSO-$d_6$) δ: 7.81 (d, $J_{3'',4''}=J_{3''',4'''}$=8 Hz, 2H, H-3", H-3'''), 7.46 (t, $J_{3',2'/3',4'}=J_{5',4'/5',6'}$=8 Hz, 2H, H-3', H-5'), 7.37 (d, $J_{2',3'}=J_{6',5'}$=8 Hz, 2H, H-2', H-6'), 7.30 (m, 5H, H-2', H-4', H-5", H-6", H-4''', H-6'''), 6.99 (t, $J_{4'',3''/4'',5''}=J_{4''',3'''/4''',5'''}$=8 Hz, 2H, H-4", H-4'''), 4.25 (s, 4H, 2CH$_2$), 2.71 (s, 3H, N—CH$_3$), 1.50 (s, 3H, CH$_3$).

4-(Bis(4-iodobenzyl) amino)-1,5-dimethyl-2-phenyl-1,2-dihydro-3H-pyrazol-3-one (5): Mp: 220-221° C.; IR (KBr, cm$^{-1}$): 1660 (C=O), 1590, 1484 (C=C), 880.1 (C—I); EI-MS (direct probe, positive EI) m/z: 635.3 [M$^+$], 508.3, 417.9; HREI-MS m/z: Calculated for $C_{25}H_{23}I_2N_3O$: 634.9930, Observed: 634.9939; $^1$H-NMR (400 MHz, DMSO-d$_6$) δ: 7.64 (d, $J_{3'',2''}=J_{5'',6''}=J_{3''',2'''}=J_{5''',6'''}$ 8 Hz, 4H, H-3", H-5", H-3''', H-5'''), 7.45 (t, $J_{3',2'/3',4'}=J_{5',6'/5',4'}$=8 Hz, 2H, H-3', H-5'), 7.27 (m, 3H, H-2', H-4', H-6'), 7.09 (d, $J_{2'',3''}=J_{6'',5''}=J_{2''',3'''}=J_{6''',5'''}$=8 Hz, 4H, H-2", H-6", H-2''', H-6'''), 4.06 (s, 4H, 2CH$_2$), 2.76 (s, 3H, N—CH$_3$), 1.72 (s, 3H, CH$_3$). $^{13}$C—NMR (100 MHz, DMSO-d$_6$) δ 164.0 (C=O), 154.0 (C-5), 138.6 (C-1", C-1'''), 135.2 (C-1'), 120.0 (C-4", C-4'''), 117.5 (C-4), 131.0 (C-2", C-6", C-2''', C-6'''), 131.0 (C-3", C-5", C-3''', C-5''') 129.0 (C-3', C-5'), 125.8 (C-4'), 123.0 (C-2', C-6') 56.5 (2CH$_2$), 36.0 (N—CH$_3$), 9.7 (CH$_3$).

4-(Bis(2-bromobenzyl) amino)-1,5-dimethyl-2-phenyl-1,2-dihydro-3H-pyrazol-3-one (6): p: 201-202° C.; IR (KBr, cm$^{-1}$): 1651 (C=O), 1590, 1492 (C=C), 1025.4 (C—Br); EI-MS (direct probe, positive EI) m/z: 543.1 [M+4]$^+$, 541.1 [M+2]$^+$, 539.02 [M$^+$], 460.1, 371.9; HREI-MS m/z: Calculated for $C_{25}H_{23}Br_2N_3O$: 539.0208, Observed: 539.0180; $^1$H-NMR (400 MHz, DMSO-d$_6$) δ: 7.55 (d, $J_{3'',4''}=J_{3''',4'''}$=7.6 Hz, 2H, H-3", H-3'''), 7.45 (t, $J_{3',2/3',4'}=J_{5',4'/5',6'}$=7.6 Hz, 2H, H-3', H-5'), 7.38 (d, $J_{2',3'}=J_{6',5'}$=7.6 Hz, 2H, H-2', H-6'), 7.27 (m, 5H, H-4', H-5", H-6", H-5''', H-6'''), 7.15 (t, $J_{4'',3''/4'',5''}=J_{4''',3'''/4''',5'''}$=7.6 Hz, 2H, H-4", H-4''') 4.25 (s, 4H, 2CH$_2$), 2.70 (s, 3H, N—CH$_3$), 1.49 (s, 3H, CH$_3$).

4-(Bis(4-bromobenzyl) amino)-1,5-dimethyl-2-phenyl-1,2-dihydro-3H-pyrazol-3-one (7): Mp: 231-232° C.; IR (KBr, cm$^{-1}$): 1666.9 (C=O), 1596, 1545, 1509 (C=C), 1007 (C—Br); EI-MS (direct probe, positive EI) m/z: 543.1 [M+4]$^+$, 541.1 [M+2]$^+$, 539.02 [M$^+$], 460.1, 371.9; HREI-MS m/z: Calculated for $C_{25}H_{23}Br_2N_3O$: 539.0208, Observed: 539.0176; $^1$H-NMR (400 MHz, DMSO-d$_6$) δ: 7.48 (m, 6H, H-3', H-5', H-3", H-5", H-3''', H-5'''), 7.24 (m, 7H, H-2', H-4', H-6', H-2", H-6", H-2''', H-6'''), 4.08 (s, 4H, 2CH$_2$), 2.76 (s, 3H, N—CH$_3$), 1.72 (s, 3H, CH$_3$). $^{13}$C—NMR (100 MHz, DMSO-d$_6$) δ 163.0 (C=O), 154.1 (C-5), 138.6 (C-1", C-1'''), 135.2 (C-1), 119.9 (C-4", C-4'''), 117.5 (C-4), 131.1 (C-2", C-6", C-2''', C-6''') 130.9 (C-3", C-5", C-3''', C-5''') 128.9 (C-3', C-5'), 125.8 (C-4'), 123.0 (C-2', C-6') 56.5 (2CH$_2$), 36.0 (N—CH$_3$), 9.7 (CH$_3$).

4-(Bis(3-bromobenzyl) amino)-1,5-dimethyl-2-phenyl-1,2-dihydro-3H-pyrazol-3-one (8): Mp: 241-242° C.; IR (KBr, cm$^{-1}$): 1679 (C=O), 1596, 1545, 1509 (C=C), 1059 (C—Br); EI-MS (direct probe, positive EI) m/z: 543.1 [M+4]$^+$, 541.1 [M+2]$^+$, 539.02 [M$^+$], 460.1, 371.9; HREI-MS m/z: Calculated for $C_{25}H_{23}Br_2N_3O$: 539.0208, Observed: 539.0205; $^1$H-NMR (400 MHz, DMSO-d$_6$) δ: 7.46 (m, 6H, H-3', H-5', H-2", H-4", H-2''', H-4'''), 7.28 (m, 7H, H-2', H-4', H-6', H-5", H-6", H-5''', H-6'''), 4.29 (s, 4H, 2CH$_2$), 2.75 (s, 3H, N—CH$_3$), 1.70 (s, 3H, CH$_3$).

Material

4-Aminoantipyrine (A) was purchased from Alfa Aesar (Heysham, UK), 3-chloro, 3-iodo, 2-iodo, and 4-iodo benzyl bromide was purchased from Mreda Technology Inc (USA) and Innochem (UAE). 2-Bromo, 4-bromo, 2-chloro and 3-bromo benzyl bromide were purchased from Innochem (UAE).

Electron impact mass spectroscopy (EI-MS), was done by using JEOLJMS-600H mass spectrometer (Japan). 300 and 400 MHz Bruker Avance NMR spectrometers (Switzerland) were used to record the NMR spectra. Melting point of the synthesized analogues were recorded by using Buchi M-560 (Japan). FTIR-8900 (Shimadzu, Japan) was used to analyze the IR spectra of the synthesized compounds through KBr disc.

Methods

Method of Preparation of Compounds 1-8:

A solution of 4-aminoantipyrine (1 mmol), $K_2CO_3$ (1 mmol), and substituted benzyl bromide (1 mmol) was prepared in DMF (2 mL), placed in a thick-walled screw capped vial in a microwave reactor at temperature 220° C., and power (max. 900 W) for 1-3 mins. Upon completion, extraction through ethyl acetate and saturated solution of lithium chloride (50:50) was carried out. Furthermore, the final products were purified through column chromatography (silica gel) with ethyl acetate and hexane as eluent.

Protocol for In-Vitro Butyryl Cholinesterase Activity

In-vitro butyryl cholinesterase inhibitory activity was performed in 96-well microplates, 0.5 mM test compound in methanol, was incubated with 20 μL butyrylcholinesterase, and 150 μL of sodium phosphate buffer of pH 8.0 for 15 minutes at 25° C. After that 10 μL of pre-prepared butyryl-thiocholine chloride (0.5 mM) substrate was added in the dark for 15 minutes, followed by the addition DTNB (0.5 mM), to produce thionitrobenzoate (TNB), whose absorbance range in 412 nm. 5-Thio-2 nitrobenzoate (TNB) (yellow color) anion was produced when thiocholine binds with DTNB which was measured in the form of absorbance in each well. Each compound was evaluated in triplicate at 0.5 mM.

Calculations of Inhibitory Activity

The enzyme inhibitory activity was calculated using the following formula:

$$\text{Percent Inhibition} = 100 - (\text{O.D. of test}/\text{O.D. of control}) \times 100$$

Where test is the enzyme activity with sample, and control is the enzyme activity without sample, and O.D. is optical density.

$IC_{50}$ Value Determination

The $IC_{50}$ values of the compounds were measured by monitoring the inhibitory effect of different concentrations ranging from 0.5-0.0125 μM for in-vitro butyryl cholinesterase activity. The $IC_{50}$ of the compounds was calculated using EZ-Fit Enzyme Kinetic Program (Perrella Scientific Inc., Amhrest, U.S.A.).

Kinetic Studies

Kinetics of two potent compounds 5 and 6 was done by using L-B reciprocal plots, designed by using GraFit software. 0.5 mM concentrations of each inhibitor, as well as control, were examined for their butyrylcholinesterase inhibitory activity using four different substrate concentrations (0.05, 0.1, 0.2, and 0.4 mM). Compound 5 show competitive inhibition, which indicates it binds with the active site of the enzyme. However, compound 6 shows non-competitive type of inhibition, which indicates it binds with the allosteric site of the enzyme.

Result and Discussion

4-Aminoantipyrine (A) and compounds 1-8 were evaluated for their in vitro enzyme inhibition activity against butyrylcholinesterase (BuChE) enzyme, results shown in table 1. Compounds 1, 2, 3, 5, 6, and 8 showed potent activities in the range of $IC_{50}$=0.0262±0.4 to 2.43±0.4 μM. In comparison to the standard drug, galantamine hydrobromide ($IC_{50}$=40.83±0.4 μM). However, compound 7, and 4-aminoantipyrine displayed lesser activity than the standard drug with $IC_{50}$=58.7±0.4 and 69.7±0.4 μM, respectively. Compound 4 was found to be completely inactive.

The limited SAR study reveals that position and nature of the halogen substituted on the phenyl ring plays a vital role in exhibiting the biological activity of the synthesized derivatives. Irrespective of the nature of halogens position 3 is found to be the most suitable in exhibiting the BuChE inhibition activity. On comparing the nature of the halogens present on the synthesized analogues 1-8, bromo is responsible for the higher activity as compared to chloro and iodo group.

In conclusion we identified 4-aminoantipyrine (A) and compound 7 as the moderate inhibitor of butyrylcholinesterase enzyme, while other derivatives 1, 2, 3, 5, 6, and 8 as potent inhibitors of butyrylcholinesterase enzyme.

TABLE 1

Structures of synthesized N,N'-disubstituted benzylamine derivatives of 4-aminoantipyrine, and their in-vitro butyrylcholinesterase (BuChE) inhibitory activity

| Structures | Butyrylcholinesterase Inhibition Activity $IC_{50} \pm SEM\ \mu M$ $Ki \pm SEM\ \mu M$ |
|---|---|
| 4-(Bis(3-chlorobenzyl)amino)-1,5-dimethyl-2-phenyl-1,2-dihydro-3H-pyrazol-3-one (1) | $IC_{50} = 0.1 \pm 0.2\ \mu M$ |
| 4-(Bis(2-chlorobenzyl)amino)-1,5-dimethyl-2-phenyl-1,2-dihydro-3H-pyrazol-3-one (2) | $IC_{50} = 0.5 \pm 0.1\ \mu M$ |

TABLE 1-continued

Structures of synthesized N,N'-disubstituted benzylamine derivatives of 4-aminoantipyrine, and their in-vitro butyrylcholinesterase (BuChE) inhibitory activity

| Structures | Butyrylcholinesterase Inhibition Activity $IC_{50} \pm SEM\ \mu M$ $Ki \pm SEM\ \mu M$ |
|---|---|
| 4-(Bis(3-iodobenzyl)amino)-1,5-dimethyl-2-phenyl-1,2-dihydro-3H-pyrazol-3-one (3) | $IC_{50} = 0.4 \pm 0.3\ \mu M$ |
| 4-(Bis(2-iodobenzyl)amino)-1,5-dimethyl-2-phenyl-1,2-dihydro-3H-pyrazol-3-one (4) | Not Active |
| 4-(Bis(4-iodobenzyl)amino)-1,5-dimethyl-2-phenyl-1,2-dihydro-3H-pyrazol-3-one (5) | $IC_{50} = 2.43 \pm 0.4\ \mu M$ $Ki = 5.67 \pm 0.5\ \mu M$ Competitive Inhibitor |

TABLE 1-continued

Structures of synthesized N,N'-disubstituted benzylamine derivatives of 4-aminoantipyrine, and their in-vitro butyrylcholinesterase (BuChE) inhibitory activity

| Structures | Butyrylcholinesterase Inhibition Activity $IC_{50} \pm SEM~\mu M$ $Ki \pm SEM~\mu M$ |
|---|---|
| 4-(Bis(2-bromobenzyl)amino)-1,5-dimethyl-2-phenyl-1,2-dihydro-3H-pyrazol-3-one (6) | $IC_{50} = 0.7 \pm 0.2~\mu M$ $Ki = 2.4 \pm 0.4~\mu M$ Non-competitive Inhibitor |
| 4-(Bis(4-bromobenzyl)amino)-1,5-dimethyl-2-phenyl-1,2-dihydro-3H-pyrazol-3-one (7) | $IC_{50} = 58.7 \pm 0.4~\mu M$ |
| 4-(Bis(3-bromobenzyl)amino)-1,5-dimethyl-2-phenyl-1,2-dihydro-3H-pyrazol-3-one (8) | $IC_{50} = 0.0262 \pm 0.4~\mu M$ |
| 4-aminoantipyrine (A) | $IC_{50} = 69.7 \pm 0.4~\mu M$ |
| Galantamine Hydrobromide (standard) | $IC_{50} = 40.83 \pm 0.4~\mu M$ $Ki = 21.5 \pm 0.7~\mu M$ Mixed type Inhibitor |

The invention claimed is:

1. A 4-aminoantipyrine derivatives selected from the group consisting of 4-(bis(3-chlorobenzyl) amino)-1,5-dimethyl-2-phenyl-1,2-dihydro-3H-pyrazol-3-one; 4-(bis(2-chlorobenzyl) amino)-1,5-dimethyl-2-phenyl-1,2-dihydro-3H-pyrazol-3-one; 4-(bis(3-iodobenzyl) amino)-1,5-dimethyl-2-phenyl-1,2-dihydro-3H-pyrazol-3-one; 4-(bis(4-iodobenzyl) amino)-1,5-dimethyl-2-phenyl-1,2-dihydro-3H-pyrazol-3-one: 4-(bis(2-bromobenzyl) amino)-1,5-dimethyl-2-phenyl-1,2-dihydro-3H-pyrazol-3-one; 4-(bis(4-bromobenzyl) amino)-1,5-dimethyl-2-phenyl-1,2-dihydro-3H-pyrazol-3-one; and 4-(bis(3-bromobenzyl) amino)-1,5-dimethyl-2-phenyl-1,2-dihydro-3H-pyrazol-3-one and a pharmaceutically acceptable salt thereof.

2. A method of treating a disease associated with the inhibition of butyrylcholinesterase enzyme, the method comprising administering to a subject in need thereof an effective amount of 4-aminoantipyrine derivative selected from the group consisting of 4-(bis(3-chlorobenzyl) amino)-1,5-dimethyl-2-phenyl-1,2-dihydro-3H-pyrazol-3-one, 4-(bis(2-chlorobenzyl) amino)-1,5-dimethyl-2-phenyl-1,2-dihydro-3H-pyrazol-3-one, 4-(bis(3-iodobenzyl) amino)-1,5-dimethyl-2-phenyl-1,2-dihydro-3H-pyrazol-3-one, 4-(bis(4-iodobenzyl) amino)-1,5-dimethyl-2-phenyl-1,2-dihydro-3H-pyrazol-3-one, 4-(bis(2-bromobenzyl) amino)-1,5-dimethyl-2-phenyl-1,2-dihydro-3H-pyrazol-3-one, 4-(bis(4-bromobenzyl) amino)-1,5-dimethyl-2-phenyl-1,2-dihydro-3H-pyrazol-3-one, and 4-(bis(3-bromobenzyl) amino)-1,5-dimethyl-2-phenyl-1,2-dihydro-3H-pyrazol-3-one and a pharmaceutically acceptable salt thereof as inhibitors of butyrylcholinesterase enzyme.

3. The method according to claim 2, wherein the disease is Alzheimer's disease.

\* \* \* \* \*